US012569315B2

(12) United States Patent
Henderson et al.

(10) Patent No.: US 12,569,315 B2
(45) Date of Patent: Mar. 10, 2026

(54) TISSUE MARKING DEVICE AND METHODS OF USE THEREOF

(71) Applicant: DFC MEDICAL LLC, Houston, TX (US)

(72) Inventors: James Robert Henderson, Lubbock, TX (US); Christen Springs, Houston, TX (US)

(73) Assignee: DFC MEDICAL LLC, Houston, TX (US)

( * ) Notice: Subject to any disclaimer, the term of this patent is extended or adjusted under 35 U.S.C. 154(b) by 0 days.

(21) Appl. No.: 18/496,702

(22) Filed: Oct. 27, 2023

(65) Prior Publication Data

US 2024/0130829 A1    Apr. 25, 2024
US 2024/0225780 A9    Jul. 11, 2024

Related U.S. Application Data

(63) Continuation of application No. 16/655,847, filed on Oct. 17, 2019, now Pat. No. 11,839,517.

(60) Provisional application No. 62/746,922, filed on Oct. 17, 2018.

(51) Int. Cl.
*A61B 17/00*        (2006.01)
*A61B 90/00*        (2016.01)

(52) U.S. Cl.
CPC .... *A61B 90/39* (2016.02); *A61B 2017/00424* (2013.01); *A61B 2090/3908* (2016.02); *A61B 2090/3966* (2016.02); *A61B 2090/3987* (2016.02); *A61B 2090/3991* (2016.02)

(58) Field of Classification Search
CPC ............ A61B 90/39; A61B 2090/3908; A61B 2090/3987; A61B 2090/3991
See application file for complete search history.

(56) References Cited

U.S. PATENT DOCUMENTS

| | | | |
|---|---|---|---|
| 5,556,410 A | | 9/1996 | Mittermeir et al. |
| 6,093,154 A | * | 7/2000 | Burek .................... A61B 90/39 |
| | | | 600/564 |
| 6,544,269 B2 | | 4/2003 | Osborne et al. |
| 6,905,484 B2 | | 6/2005 | Buckman et al. |
| 8,437,834 B2 | | 5/2013 | Carr, Jr. |
| 8,718,745 B2 | | 5/2014 | Burbank et al. |
| 9,044,162 B2 | | 6/2015 | Jones et al. |
| 10,524,875 B2 | | 1/2020 | Hermann et al. |
| 10,959,802 B1 | | 3/2021 | Henderson et al. |
| 11,839,517 B2 | * | 12/2023 | Springs ................. A61B 90/39 |

(Continued)

FOREIGN PATENT DOCUMENTS

| | | |
|---|---|---|
| WO | 2020068658 A1 | 4/2020 |
| WO | 2021217007 A1 | 10/2021 |

*Primary Examiner* — Katherine M Shi
*Assistant Examiner* — Mohammed S Adam
(74) *Attorney, Agent, or Firm* — BakerHostetler

(57) ABSTRACT

Disclosed herein are tissue marking devices and methods that enables marking a target tissue more than 24 hours prior to surgery. The tissue marking device includes a hook assembly having a compressed configuration and a deployed configuration and a handle assembly for positioning the hook assembly in a targeted tissue. The hook assembly may include a hook body comprising at least two hooks and a thread connected to the hook body. The handle assembly may include a handle body, a needle having a lumen, and a stylet having a lumen.

19 Claims, 12 Drawing Sheets

(56)        References Cited

U.S. PATENT DOCUMENTS

| | | | |
|---|---|---|---|
| 2003/0233125 A1* | 12/2003 | Kaplan | A61N 1/08 |
| | | | 977/880 |
| 2004/0097981 A1 | 5/2004 | Selis | |
| 2005/0143674 A1 | 6/2005 | Burbank et al. | |
| 2009/0000629 A1 | 1/2009 | Hornscheidt et al. | |
| 2010/0030149 A1 | 2/2010 | Carr, Jr. | |
| 2010/0204570 A1 | 8/2010 | Lubock | |
| 2011/0071431 A1* | 3/2011 | Speeg | A61B 90/39 |
| | | | 600/567 |
| 2011/0152611 A1 | 6/2011 | Ducharme et al. | |
| 2011/0319932 A1 | 12/2011 | Avelar et al. | |
| 2014/0309522 A1* | 10/2014 | Fullerton | A61B 90/39 |
| | | | 600/424 |
| 2017/0296294 A1 | 10/2017 | Hermann et al. | |
| 2018/0035914 A1 | 2/2018 | Fullerton et al. | |
| 2019/0374277 A1* | 12/2019 | Bagwell | A61B 18/1492 |
| 2020/0121414 A1 | 4/2020 | Springs et al. | |

* cited by examiner

200

Insert needle into patient

204

Check location of needle relative to target tissue

206

Unlock locking mechanism

208

Depress plunger

210

Release plunger and remove needle and stylet from patient

212

300

TISSUE MARKING DEVICE AND METHODS OF USE THEREOF

CROSS-REFERENCE TO RELATED PATENT APPLICATION

This patent application is a continuation of U.S. application Ser. No. 16/655,847, entitled "TISSUE MARKING DEVICE AND METHODS OF USE THEREOF," filed Oct. 17, 2019, which claims the benefit under 35 U.S.C. § 119(e) of U.S. patent application Ser. No. 62/746,922, entitled "TISSUE MARKING DEVICE AND METHODS OF USE THEREOF," filed on Oct. 17, 2018, each of which is incorporated herein by reference in its entirety.

FIELD OF THE INVENTION

The present invention relates generally to surgical tissue identification and removal, and more specifically, to a marking specific tissues within a breast at a time prior to removal of the tissue by surgery.

BACKGROUND

Tissue marking is used to externally indicate to a surgeon which tissue is to be tracked or removed, such as a tumor or mass. For example, after a breast biopsy determining that a tissue is cancerous and needs to be removed, a tissue marking device with a single hook attached to a rigid wire is inserted such that the wire extends outside the breast. The tissue marking device provides an external indication of the location of the tumor for the surgeon.

However, the standard tissue marking device has many limitations. Using current technology, the tissue must be marked on the same day, just prior to surgery to avoid displacing the hook. This leads to an extended time that the patient must be at the hospital. Coordinating schedules of Radiology, Surgery, and the Operating room staff leads to inefficiencies and affects patient satisfaction.

Accordingly, there is a need for a tissue marking device that is not prone to movement once in place such that it may be placed in a patient more than 24 hours before a surgery to remove the tissue.

BRIEF SUMMARY

The disclosure provides for a tissue marking device and methods of marking a tissue. The tissue marking device may include a hook assembly having a compressed configuration and a deployed configuration and a handle assembly for positioning the hook assembly in a targeted tissue. In an aspect, the hook assembly may include a hook body comprising at least two hooks, a retention mechanism, and a thread connected to the hook body. In one aspect, a metal thread may be welded, crimped, swagged, kinked, UV bounded, laser welded, or joined by any of means suitable for bonding metals to the proximal end of the hook body to form the hook assembly. In another aspect, the handle assembly may include a handle body having a proximal end and a distal end, a plunger having a locking mechanism, a needle having a lumen with an open first end and a second end, and a stylet having a lumen with an open first end and a second end. In an aspect, the hook body and the stylet are within the lumen of the needle and the thread is within the lumen of the stylet when the hook assembly is in the compressed configuration.

Further provided herein is a method of marking a target tissue in a patient. In an aspect, the method may include inserting a needle of the tissue marking device into a patient, confirming the location of the needle such that the hook body is near the target tissue, unlocking the locking mechanism on the handle body, depressing the plunger to extend the hook body past the needle and open the at least two hooks and retention mechanism to embed the hook body in the target tissue, and removing the needle and the stylet from the patient.

In another aspect, the method of marking a target tissue in a patient may include implanting a hook assembly of a tissue marking device into a target tissue of a patient. In this aspect, the hook assembly is operable to absorb compression without migrating more than 1 cm within the target tissue. In another aspect, the hook assembly is operable to allow the patient to have surgery to remove the hook assembly on a separate day from implantation.

Additional aspects and features are set forth in part in the description that follows, and will become apparent to those skilled in the art upon examination of the specification or may be learned by the practice of the disclosed subject matter. A further understanding of the nature and advantages of the disclosure may be realized by reference to the remaining portions of the specification and the drawings, which forms a part of this disclosure.

DESCRIPTION OF THE DRAWINGS

The description will be more fully understood with reference to the following figures, which are presented as variations of the disclosure and should not be construed as a complete recitation of the scope of the disclosure, wherein.

DETAILED DESCRIPTION

Figure 1A:
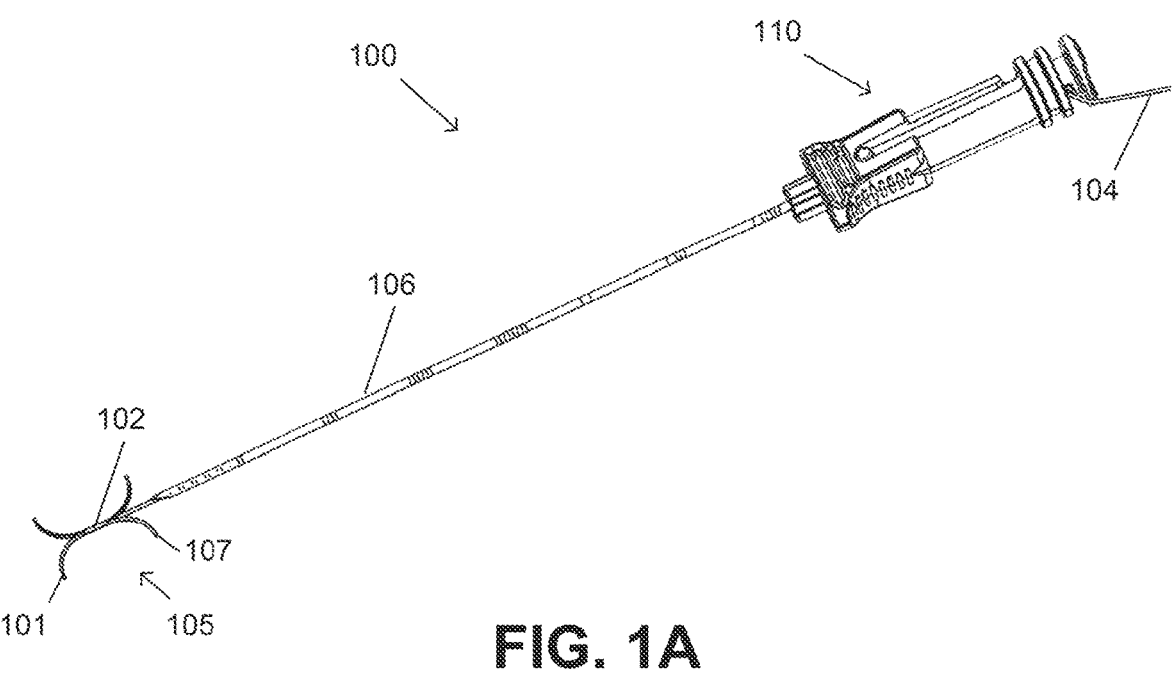
FIG. 1A is a perspective view of the tissue marking device in one variation.

The tissue marking device and method of use will be understood, both as to its structure and operation, from the accompanying drawings, taken in conjunction with the accompanying description. It is noted that, for purposes of illustrative clarity, certain elements in various drawings may not be drawn to scale. Several variations of the device are presented herein. It should be understood that various components, parts, and features of the different variations may be combined together and/or interchanged with one another, all of which are within the scope of the present application, even though not all variations and particular variations are shown in the drawings. It should also be understood that the mixing and matching of features, elements, and/or functions between various variations is expressly contemplated herein so that one of ordinary skill in the art would appreciate from this disclosure that the features, elements, and/or functions of one variation may be incorporated into another variation as appropriate, unless described otherwise.

For purposes of this description, "distal" refers to the end extending into a body and "proximal" refers to the end extending out of the body.

For purposes of this description "connected to" includes two components being directly connected or indirectly connected with intervening components.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term.

In traditional lumpectomy procedures, a localization wire is placed by a radiologist on the same day of the surgical procedure. This protocol requires the patient to go through two procedures in two separate departments on the same day. For the patient, this leads to increased anxiety levels and a reduction in satisfaction. For the facility, this can lead to lost revenue from scheduling difficulties. Wire-based localization technologies are also mechanically deficient. Wires can move during the long procedure day and are uncomfortable and awkward for the patient. It is not possible to schedule the radiological and surgical procedures on separate days using wire-based localization.

Capital equipment technologies require the use of expensive equipment (i.e. capital) to separate the procedure days. For example, these capital equipment systems use expensive technology like radar or magnets, combined with an external hardware system to localize the lesion. These technologies are expensive and have barriers to entry for the user. The facility must absorb the cost of the capital component to implement the technology and the cost of the actual treatment materials exceeds the available reimbursement. There is currently no simple, "low-cost" and/or single-use solution for breast lesion localization to be treated on a separate day from surgery.

The disclosed tissue marking device and methods of use thereof provides for the rapid marking of tissue more than 24 hours prior to the surgery. The tissue marking device provides a "low-cost" and single-use alternative to capital equipment technologies and provides for the separation of treatment days as an alternative to wire-based localization. For example, the tissue marking device uses a hook assembly with superior pull force strength to minimize migration and absorb compression and uses a flexible thread instead of a wire. In particular, the hook assembly is operable to absorb compression without migrating more than 1 cm within the target tissue. These features, described in detail below, allow for the device to be placed on a separate day than the surgery to remove the target tissue. In addition, the tissue marking device allows the patient to move without discomfort or risk of dislocating the hook marking the target tissue. Moreover, the tissue marking device is a simple, easy to use, handheld device for marking target tissue and does not require investment of any expensive equipment such as radar or magnets. The tissue marking device is an economically effective solution for the clinical, scheduling, and patient satisfaction issues associated with the current standard. In some variations, the tissue marking device overcomes one or more of the above-listed problems commonly associated with conventional wire marker devices and capital equipment technologies.

FIG. 1 depicts a side view of a tissue marking device for marking a target tissue in one variation. In various variations the target tissue may be within a breast. Examples of target tissue include lesions, cancerous and non-cancerous tumors, or masses.

Figure 1B:
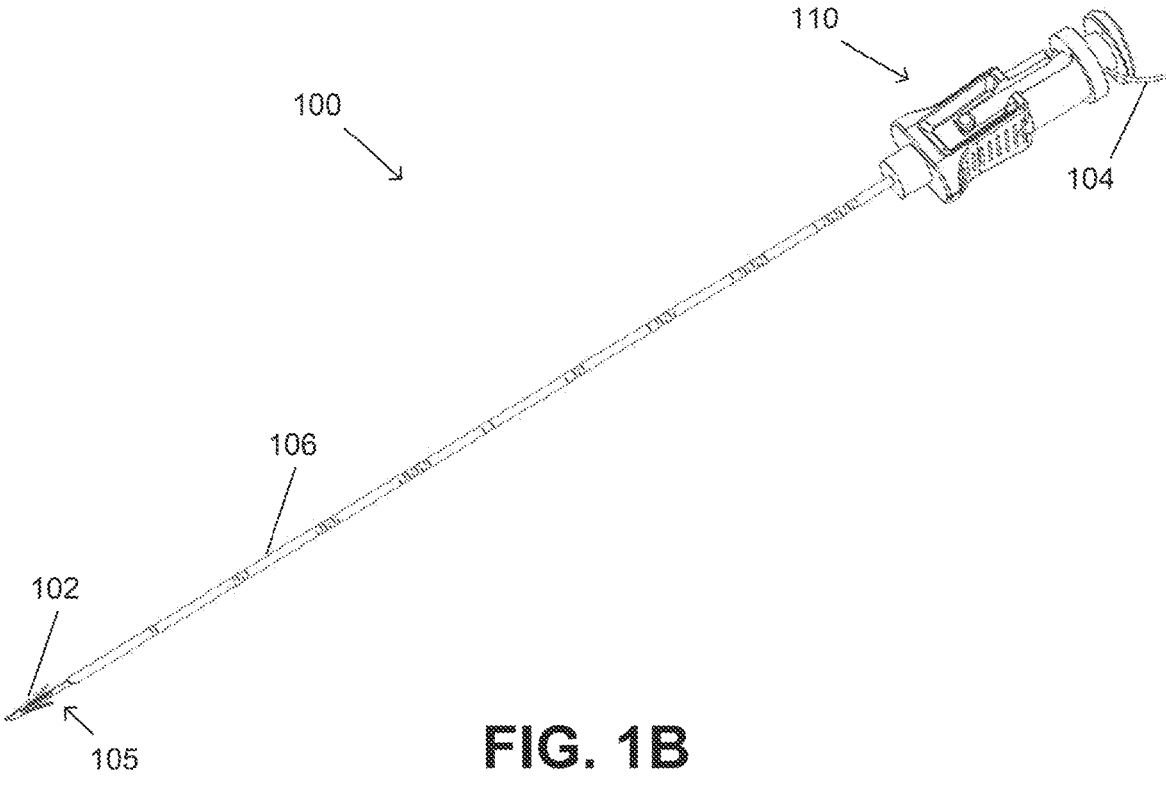
FIG. 1B is a perspective view of the tissue marking device in one variation.

As seen in FIGS. 1A-1B, the tissue marking device 100 includes a handle assembly 110 and a hook assembly 105. In a variation, the handle assembly 110 includes a handle body 111, a needle 106, and a stylet 108. The hook assembly 105 includes a hook body 102 connected to a thread 104. The handle assembly 110 is used insert and deploy the hook assembly 105 at the target tissue and allow for easy removal of the handle assembly 110 once the hook assembly 105 is deployed. The hook assembly remains in the patient, with the hook body 102 located at the target tissue and the thread 104 extending from the hook body to outside the patient's body. In a variation, the thread 104 may be flexible such that it can remain external to the body more than 24 before surgery without risking migration of the hook body 102 if the thread 104 is touched by the patient. In another variation, the hooks 101 on the hook body 102 may prevent unintended migration of the hook body 102 after the hook assembly 105 has been placed and deployed.

Figures 2A, 2B:
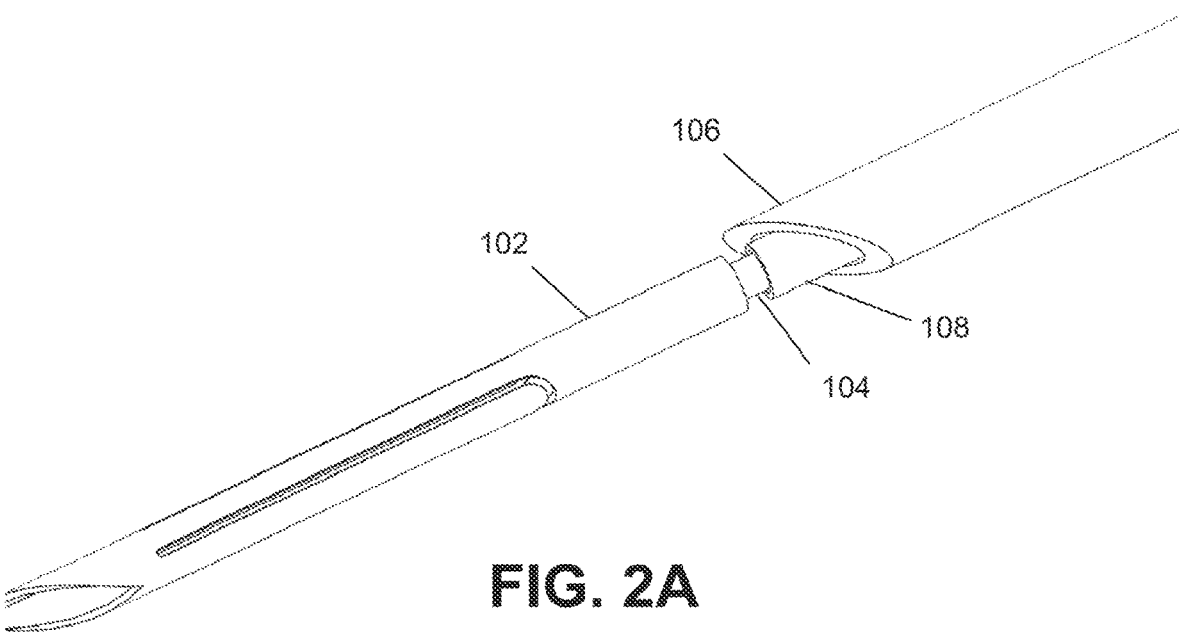
FIG. 2A is a view of the distal end of the tissue marking device with the hook body in the compressed configuration as it would be seen if inside the needle, in one variation.
FIG. 2B is a view of the hook body in the compressed configuration as it would be seen if inside the needle, in one variation.

The hook assembly 105, by way of the hook body 102, can be in a compressed configuration or a deployed configuration. In the compressed configuration, the hooks 101 and/or retention mechanism 107 of the hook body 102 are compressed together such that the hook assembly 105 can be loaded and fit within the lumen of the needle 106. For example, the hook body 102 in the compressed configuration generally looks like a tube. In a variation, the hooks 101 and/or retention mechanism 107 of the hook body 102 are forcibly compressed by the lumen of the needle 106. FIGS. 2A-2B show the hook body 102 in the compressed configuration, in some variations, as it would be seen if fully contained within the needle 106 of the handle assembly 110.

Figure 2C:
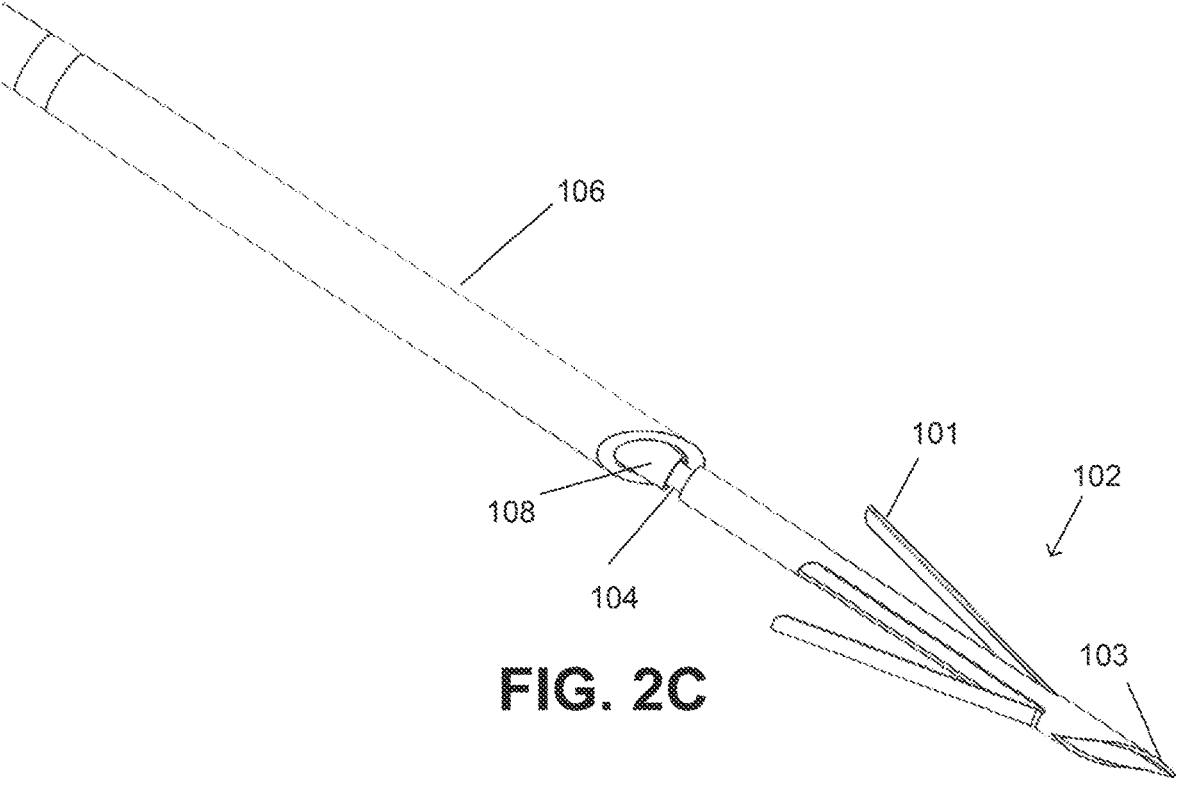
FIG. 2C is a view of the distal end of the tissue marking device with the hook assembly in the deployed configuration, in one variation.
Figure 2D:
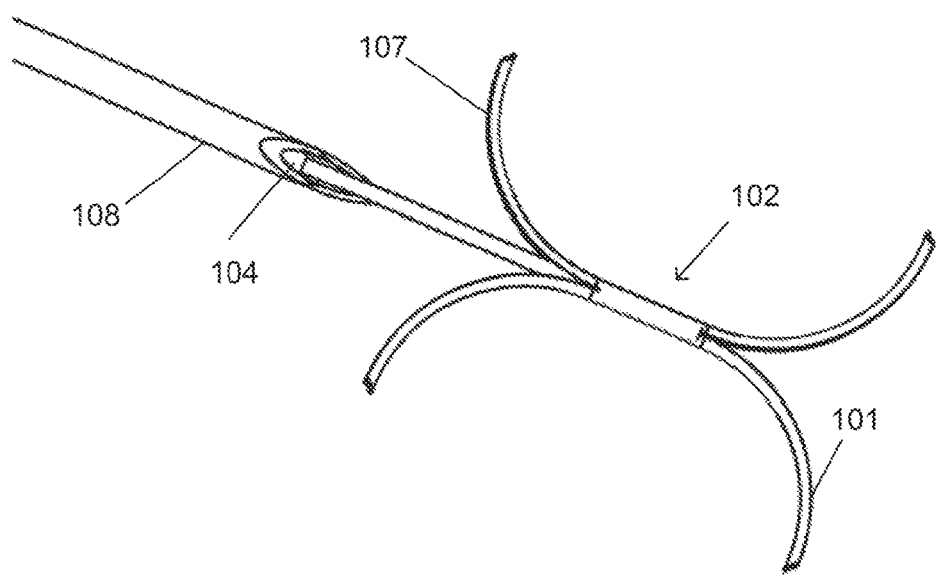
FIG. 2D is a view of the distal end of the tissue marking device with the hook assembly in the deployed configuration, in one variation.

Once the handle assembly 110 pushes the stylet 108, the stylet 108 pushes the hook body 102 out of the needle 106 and the hooks 101 and/or retention mechanism 107 expand or deploy because they are no longer compressed by the needle 106. FIGS. 2C-2D show the hook body 102 in the deployed configuration, in some variations, prior to the handle assembly 110 being removed.

The hook body 102 has a proximal end and a distal end. The hook body 102 may include at least two hooks 101 at the distal end of the hook body 102. FIGS. 3A-3F show non-limiting examples of distal hook shapes, numbers, and configurations that may be included on the hook body. In a variation, the at least two hooks 101 may be separated by 180°. In a variation, the at least two hooks 101 may be separated by 120°. In a variation, the at least two hooks 101 may be separated by 90°. In a variation, the at least two hooks 101 may be separated by 45°. In a variation, the at least two hooks 101 may be separated by a combination of 180°, 120°, 90° and/or 45°. In some variations, the at least two hooks 101 may be equidistant from one another.

Figure 3A:
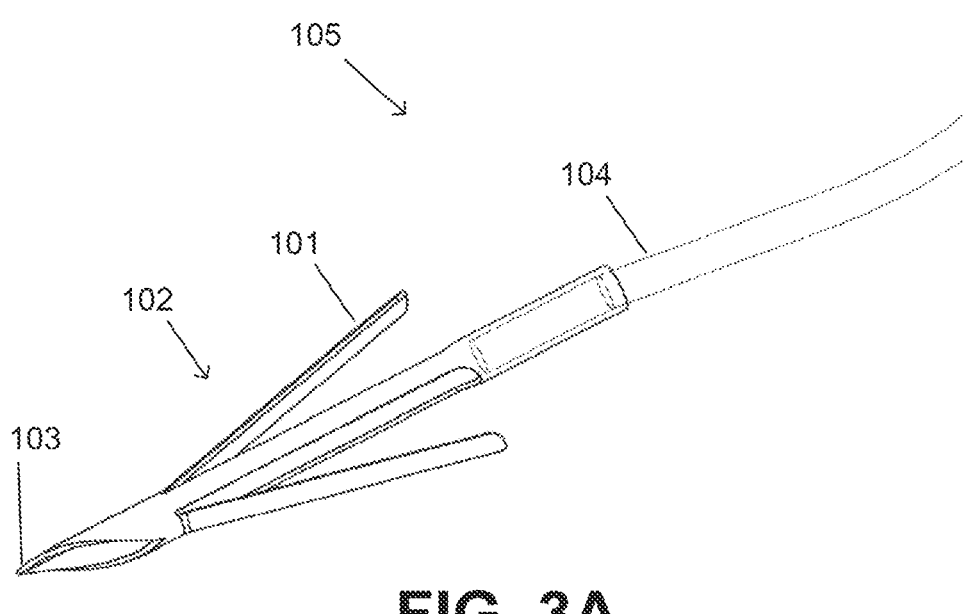
FIG. 3A is a side view of a non-removable hook assembly with three hooks in one variation.
Figure 3B:
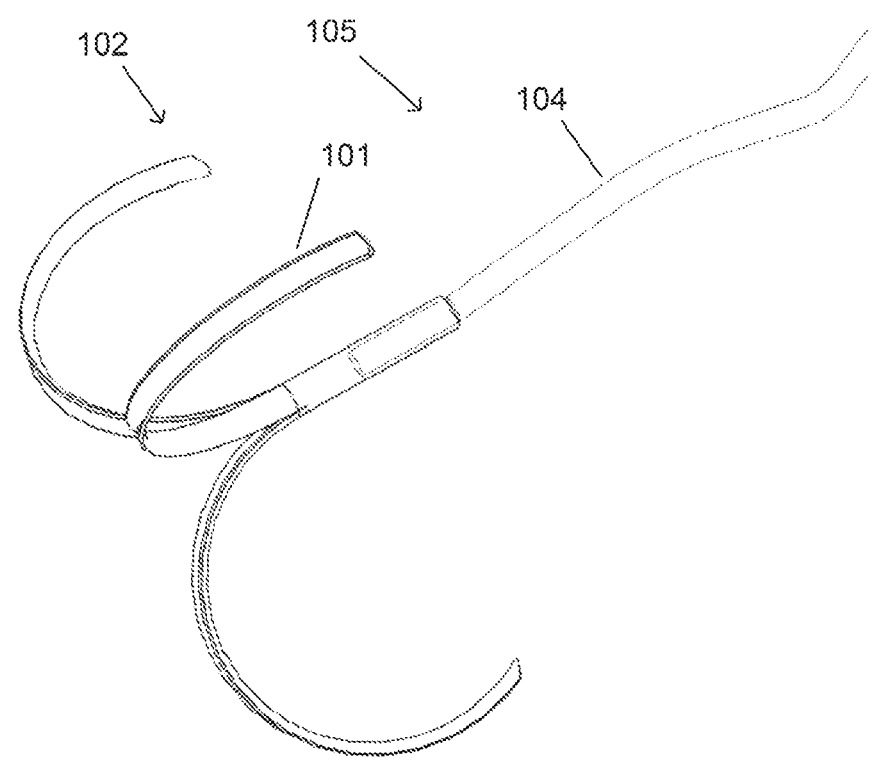
FIG. 3B is a side view of a hook assembly with three hooks in one variation.
Figure 3C:
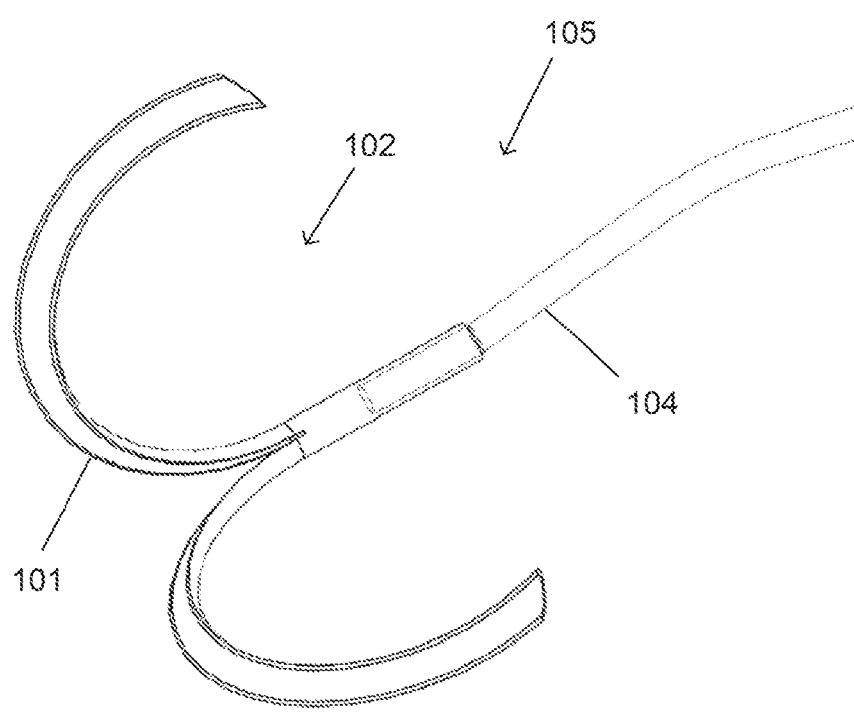
FIG. 3C is a side view of a hook assembly with two hooks in a 90° configuration in one variation.
Figure 3D:
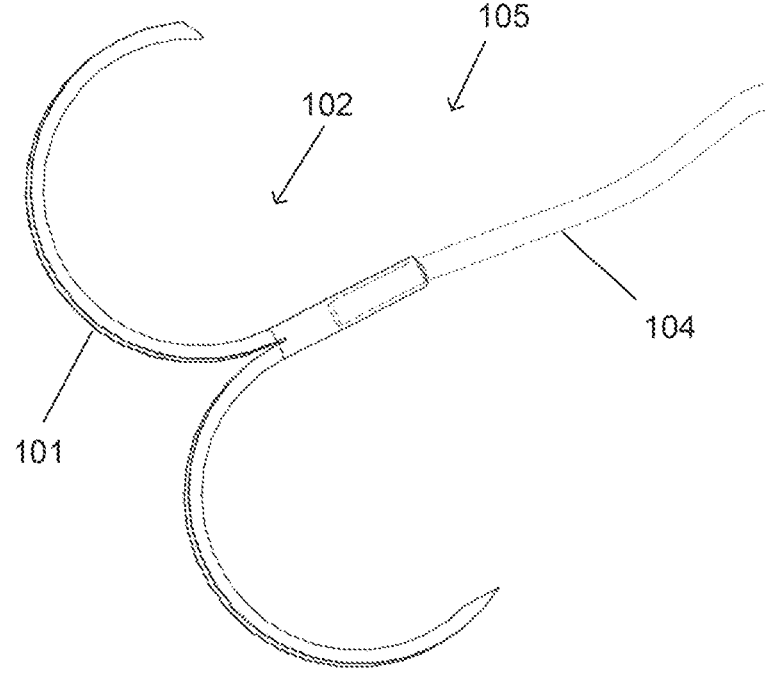
FIG. 3D is a side view of a hook assembly with two hooks in a 180° configuration in one variation.

In some variations, the hook body may include at least two hooks 101. In some variations, the hook body may include at least three hooks 101. In some variations, the hook body may include at least four hooks 101. In some variations, the hook body may include at least five hooks 101. In a variation, the hook body 102 may include three hooks 101, as seen in FIG. 3A or FIG. 3B. In a variation, two of the hooks may be separated by 180° while a third hook may be 90° from each of the other two hooks. In a variation, three hooks may be separated by 90° or 45°. In another variation, the hook body 102 may include two hooks, as seen in FIG. 3C, where the two hooks 101 are separated by 90°. In yet another variation, the hook body 102 may include two hooks, as seen in FIGS. 3D-3F, where the two hooks 101 are separated by 180°.

The at least two hooks 101 may have a straight configuration, a rounded configuration, a curved configuration, or any configuration sufficient to retain the hook body within the target tissue and absorb compression forces. In a variation, the hooks 101 may have a rounded or curved configuration, as seen in FIGS. 3E-3F. In a variation, the hooks 101 may be offset from the hook body by about 45°. In a variation, the hooks 101 may be offset from the hook body by about 90°. FIG. 3A is an example of a hook body 102 with hooks 101 in a straight configuration and FIGS. 3B-3D are examples of a hook body 102 with hooks 101 in a curved configuration. In one variation, the hook body 102 may further include a pointed distal end 103 extending past the hooks 101.

In a variation, the hook body may be non-removable. In other variations, the hook body may not be retracted, repositioned, or adjusted once deployed in the target tissue. In this variation, the hook assembly 105 may not be removed from the body except through surgery. The handle assembly 110 may not be used to remove or re-place the hook assembly 105. The hook body may not include any sharp ends that would otherwise facilitate movement of the hook assembly within the tissue.

Figure 3E:
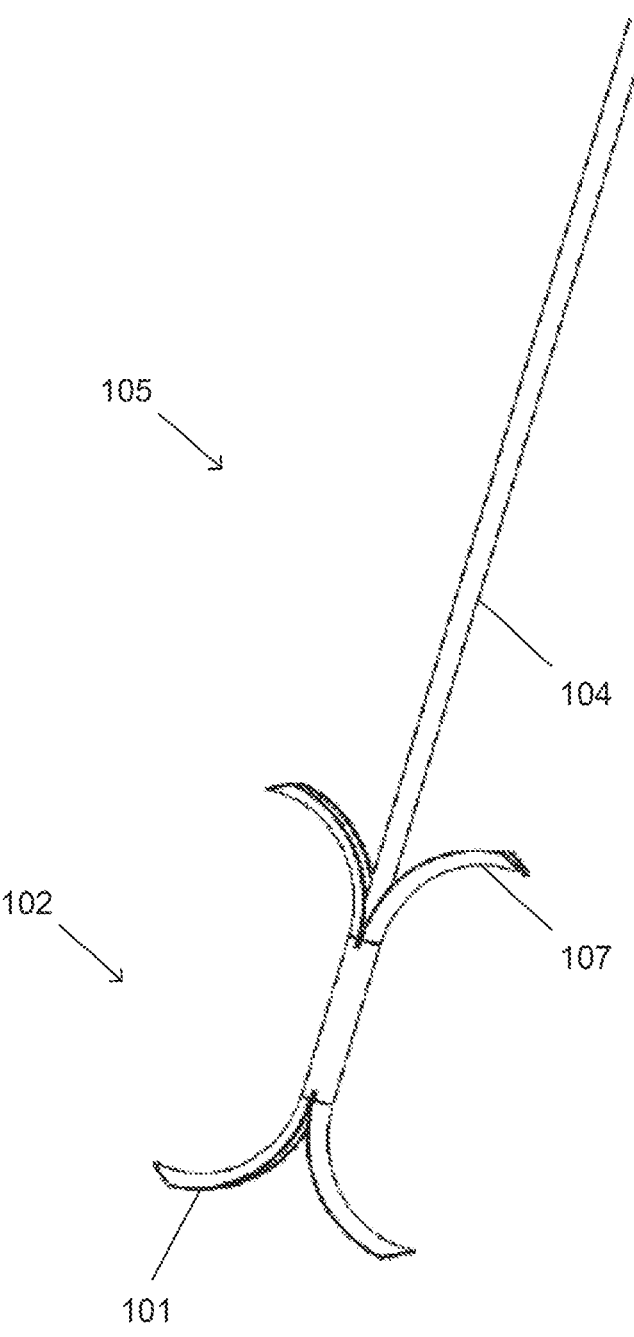
FIG. 3E is a side view of a hook assembly with two hooks in a 180° configuration and a retention mechanism with two proximal hooks in one variation.
Figure 3F:
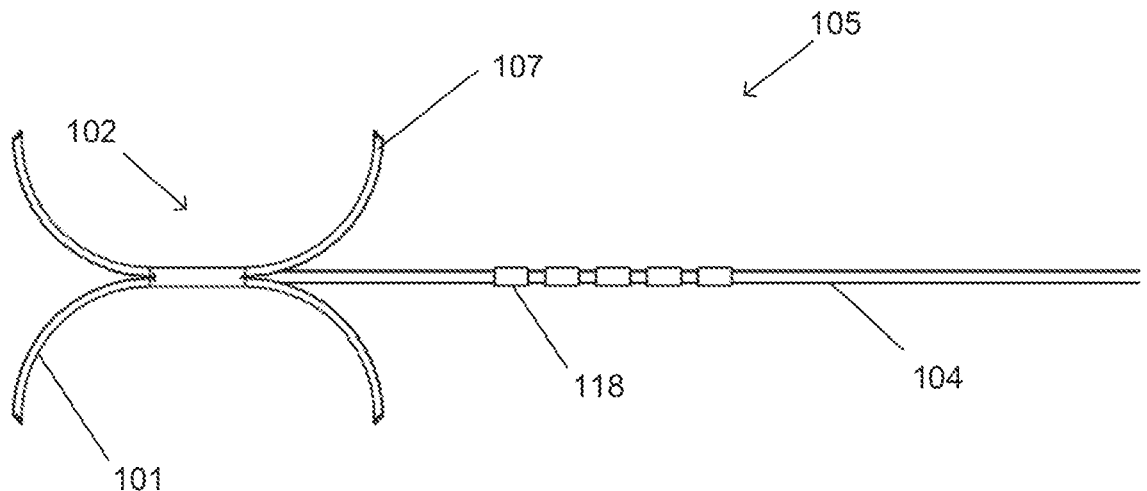
FIG. 3F is a side view of a hook assembly with two hooks in a 180° configuration and a retention mechanism with two proximal hooks in one variation.

To aid in restricting migration of the hook assembly 105, the hook body 102 may further include a retention mechanism 107 at the proximal end of the hook body 102, as seen in FIGS. 3E-3F. The retention mechanism may prevent the hook body 102 or hook assembly 105 from retracting back into the needle 106 once the hook assembly has been deployed. In addition, the retention mechanism may prevent the hook body 102 or hook assembly 105 from migrating once the hook assembly has been deployed and the handle assembly has been removed. This may allow the hook assembly 105 to remain in the patient for an extended period of time, such that the placement of the hook assembly may occur on a separate day from the surgery to remove the target tissue.

The retention mechanism 107 may have any shape or structure that absorbs compression, facilitates retention of the hook assembly 105 within the target tissue, and prevents the hook body 102 from being retracted into the needle 106 or migrating within the target tissue. In some variations, the retention mechanism 107 may have a rounded hook shape, curved hook shape, a straight hook shape, an elbow shape, or a T-shape. In a variation, the retention mechanism 107 may include one proximal hook. In a variation, the retention mechanism 107 has a rounded or curved hook shape, as seen in FIGS. 3E-3F. In a variation, the retention mechanism 107 may include two proximal hooks. In a variation, the retention mechanism 107 may include three proximal hooks. In a variation, the retention mechanism 107 may include four proximal hooks. The retention mechanism 107 may be laser cut from the same nitinol tube that the hooks are cut, such that the hooks, retention mechanism, and hook body are a single element. In a variation, the retention mechanism 107 may be the same length as the hooks 101. In a variation, the retention mechanism 107 may be shorter than the hooks 101. In a variation, the retention mechanism 107 may be longer than the hooks 101.

In a variation, the hook body 102 may include two distal hooks 101 and a retention mechanism 107 with two proximal hooks, generally forming a four hook/arm configuration, or an "H" configuration, as seen in FIGS. 3E-3F. In this variation, the hook body optimizes resistance to migration while also allowing flex inside the tissue during normal patient movements. In an example, the arms flex when compressed with near zero migration. In a variation, the two distal hooks and the two proximal hooks are located in the same plane. In another variation, the two distal hooks and the two proximal hooks are offset by an angle such that they are not in the same plane. For example, the anterior and posterior side of the hooks may help with compression from the top and bottom of the breast. In another variation, two 2D/planner elements containing one distal hook and one proximal hook may be heat set to the desired bend radius and bonded together at the apex.

The hook body allows for the hook assembly to absorb compression forces without migrating a distance that would require re-localization by re-implantation of the hook assembly. In a variation, the hook assembly is operable to allow the patient to have surgery to remove the hook assembly on a separate day from localization/implantation. The ability to absorb compression forces may permit the patient to participate in normal activity between the time of localization/implantation of the hook assembly and the time of surgery to remove the target tissue. Non-limiting examples of normal activity include sleeping (face down if desired), rolling over, sexual activity, taking care of loved ones (for example, kids), exercising, accidental bumping, and/or lifting heaving objects.

The hook assembly 105, by way of the hook body 102, is operable to absorb compression forces without migrating more than 1.5 cm from the original placement within the target tissue. In a variation, the hook assembly is operable to absorb compression without migrating more than 1 cm within the target tissue. In a variation, the hook assembly is operable to absorb compression without migrating more than 8 mm within the target tissue. In a variation, the hook assembly is operable to absorb compression without migrating more than 5 mm within the target tissue. In a variation, the hook assembly is operable to absorb compression without migrating more than 3 mm within the target tissue. In a variation, the hook assembly is operable to absorb compression without migrating more than 2 mm within the target tissue. In a variation, the hook assembly is operable to absorb compression without migrating more than 1 mm within the target tissue. In a variation, the hook assembly is operable to absorb compression without migrating more than 0.5 mm within the target tissue.

In a variation, the hook body 102 may have a length of 2 mm to 8 mm in the compressed configuration. In a variation, the hook body has a length of at least 2 mm. In a variation, the hook body has a length of at least 3 mm. In a variation, the hook body has a length of at least 4 mm. In a variation, the hook body has a length of at least 5 mm. In a variation, the hook body has a length of at least 7 mm. When in the compressed configuration, the hook body 102 has a diameter sufficient to fit within the lumen of a needle 106. In a variation, the hook body 102 may have a diameter of less than 1 mm in the compressed configuration. In a variation, each hook 101 may have a length of at least 1 mm. In a variation, each hook 101 may have a length of at least 2 mm. In a variation, each hook 101 may have a length of at least 3 mm. In a variation, each hook 101 may have a length of at least 4 mm. In a variation, each hook 101 may have a diameter of less than 1 mm. In a variation, each hook 101 may have a diameter of less than 1 mm. In a variation, each hook 101 may have a diameter of less than 0.75 mm. In a variation, each hook 101 may have a diameter of less than 0.5 mm. In a variation, the retention mechanism 107 may have a length of at least 1 mm. In a variation, the retention mechanism 107 may have a length of at least 3 mm.

In a variation, the hook body 102 may be formed from a tube that has been laser cut to form the hooks 101. In this variation, the hooks 101 and the hook body 102 are a single element. Therefore, the hooks 101 may be integral to the hook body 102 and do not need to be attached together or attached to the hook body. This may allow the hook body 102 to take the shape of a tube when in the compressed configuration. Without being limited to a particular theory, laser cutting the hooks 101 into the hook body 102 allows for the hook body 102 to have a compressed configuration in the shape of a tube and a deployed configuration with the hooks 101 expanded, for example, as seen in FIGS. 2A and 2C. The hooks 101 may be pre-formed in the deployed configuration and may need to be physically compressed to be in the compressed configuration, such as being compressed by the lumen of the needle 106. In a variation, the hook body 102 may be formed from a nitinol tube.

In another variation, the hook body 102 may be formed from a tube that has been laser cut to form the hooks 101 and retention mechanism 107. In this variation, the hooks 101, the retention mechanism 107, and the hook body 102 are a single element. In some examples, the hooks 101 and retention mechanism 107 have the same shape, and may generally form four hooks/arms cut from a single tube, as seen in FIG. 3E. Therefore, the hooks 101 and retention mechanism 107 may be integral to the hook body 102 and do not need to be attached together or attached to the hook body. This may allow the hook body 102 to take the shape of a tube when in the compressed configuration. Without being limited to a particular theory, laser cutting the hooks 101 and retention mechanism 107 into the hook body 102 allows for the hook body 102 to have a compressed configuration in the shape of a tube and a deployed configuration with the hooks 101 and retention mechanism 107 expanded, for example, as seen in FIGS. 2B and 2D. The hooks 101 and retention mechanism 107 may be pre-formed in the deployed configuration and may need to be physically compressed to be in the compressed configuration, such as being compressed by the lumen of the needle 106. In a variation, the hook body 102 with integral hooks 101 and retention mechanism 107, may be formed from a nitinol tube.

In a variation, the hook body 102 may include at least one radiopaque marker. In some variations, the hooks 101 may include a radiopaque marker. In other variations, the hook body 102 itself may be used as a radiopaque marker. It will be appreciated that the radiopaque markers may be configured to communicate a set distance to further facilitate the measurement of target tissue, to distinguish between multiple marked tissues, to demonstrate the distance of the hook from the targeted lesion, or indicate a distance from the hook body to a biopsy marker clip. It will be appreciated that any arrangement of radiopaque markers is contemplated.

The hook assembly 105 further includes a thread 104 connected to the hook body 102. The thread 104 may be connected to the hook body 102 such that it remains attached to the hook body 102 when the hook assembly 105 is embedded in a targeted tissue. In some variations, the thread 104 may be welded, crimped, swagged, kinked, UV bounded, laser welded, or joined by any of means suitable for bonding metals onto the hook body 102.

The thread may be impervious to heat, completely flexible, resistant to cutting, provide a secure connection to the hook body, viewable on imaging, include marker bands, and have a proximal end that can be secured to the patient's breast. In some variations, the thread does not have to be secured to breast. In some examples, the thread may eliminate transection concern while providing heat resistance and optimal strength during surgery. The thread may be flexible or non-rigid such that it may prevent the hook body from unintentionally moving or being driven past the target tissue. In a variation, the thread 104 may be flexible yet strong. For example, the thread 104 can be flexible such that it can bend when outside the body and therefore not be at risk of being moved inside the body if touched or bumped outside the body of the patient. The thread 104 can be heat resistant such that it is not at risk of being severed if near a cauterizer and can be tough enough to not be at risk of being cut by a scalpel. Non-limiting examples of the material that may make up the thread include chromium cobalt, stainless steel, nitinol, and Kevlar. In a variation, the thread 104 is a metal thread. In one variation, the thread is made of chromium cobalt or a cobalt-chrome alloy. In another variation, the thread is made of nitinol.

The thread 104 may be located within the lumen of the stylet 108, the lumen of the needle 106, and/or through the handle body/plunger when the hook assembly 105 is loaded within the handle assembly 110 prior to deployment. The thread 104 may have a length of at least the length of the needle 106. In a variation, the thread 104 has a length so that it extends out of the second ends of the needle 106 and stylet 108 respectively. The thread 104 may have a length that is sufficient to extend through the breast and extend outside the body of the patient. In a variation, the thread 104 has a length of at least 5 cm. In a variation, the thread 104 has a length of at least 8 cm. In a variation, the thread 104 has a length of at least 10 cm. In a variation, the thread 104 has a length of at least 12 cm. In a variation, the thread 104 has a length of at least 14 cm. In a variation, the thread 104 has a length of at least 16 cm. In a variation, the thread 104 has a length of at least 20 cm. The thread 104 may have a diameter sufficient to fit through the lumen of the stylet 108 which is in the lumen of the needle 106. In a variation, the thread 104 may have a diameter of less than 1 mm. In a variation, the thread 104 may have a diameter of less than 0.5 mm. In a variation, the thread 104 may have a diameter of less than 0.25 mm.

Different variations of the hook assembly 105 may include different lengths of thread 104. For example, the tissue marking device 100 may be sized to the patient. In some variations, the excess thread 104 may be attached to the patient. For example, excess thread 104 may be wound and attached to the skin of the patient with an adhesive.

In a variation, the thread 104 may further include one or more radiopaque markers. In some variations, the radiopaque marker may be a band, a ball, or a knot in the thread 104. In some variations, the radiopaque marker may be at the point the thread 104 connects to the hook body 102. In other variations, the radiopaque marker may be at a point along the length of the thread 104. For example, a radiopaque marker may be located both at the hook body 102 and on the thread 104 about 0.5 to 2 cm away from the connection point to the hook body 102, depending on the length of the hook body in the compressed configuration.

In other variations, the thread 104 may include a series of marker bands 118 along a length of the thread, as seen for example in FIG. 3F. The marker bands may be raised from the thread such that a surgeon may be able to physically feel the marker bands. In addition, the marker bands may provide a surface to push against the hook body and/or other marker bands when the hook body is pushed out of the needle by the stylet. For example, the distal most marker band may push the hook body without any slack in between with the thread and the series of marker bands may be as close together as needed so they are all pushing on each other with no slack in the thread. In some variations, the marker bands 118 may be placed such that the distal most marker band is a set distance from the proximal end of the hook body 102 when in the compressed configuration. For example, the marker bands 118 may be placed such that the distal most marker band is about 0.5 mm, 1 mm, 2 mm, or 3 mm from the proximal end of the hook body 102 when in the compressed configuration. In other variations, the marker bands 118 may be placed on the thread 104 such that the distal most marker band is a set distance from where the thread connects to the hook body 102 (i.e. the center of the hook body). For example, the marker bands 118 may be placed on the thread 104 such that the distal most marker band is 0.5 cm to 2 cm from where the thread connects to the hook body 102 (i.e. the center of the hook body), depending on the length of the hook body in the compressed configuration. In at least one example, the marker bands 118 are placed on the thread 104 such that the distal most marker band is 1 cm from where the thread connects to the hook body 102.

In a variation, the thread may include 1 marker band. In a variation, the thread may include at least 2 marker bands. In a variation, the thread may include at least 3 marker bands. In a variation, the thread may include at least 4 marker bands. In a variation, the thread may include at least 5 marker bands. In a variation, the thread may include at least 6 marker bands. The marker bands 118 may be separated from each other by a set distance. For example, each marker band may be separated by 0.5 mm, 1 mm, 2 mm, or 3 mm. It will be appreciated that the radiopaque markers are configured to communicate a set distance to further facilitate the measurement of target tissue, to distinguish between multiple marked tissues, to demonstrate the distance of the hook from the targeted lesion, or to indicate a distance from the hook body to a biopsy marker clip. It will be appreciated that any arrangement of radiopaque markers is contemplated.

Figure 4A:
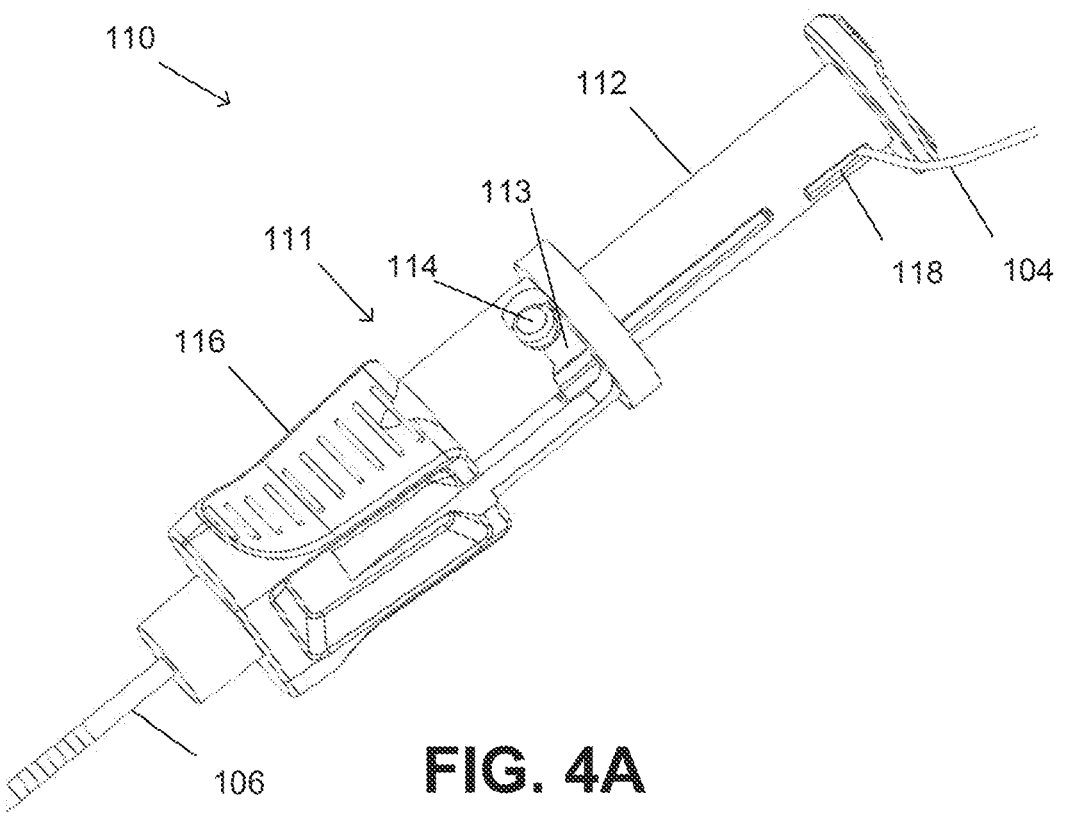
FIG. 4A is a side view of a handle assembly in the loaded position in one variation.
Figure 4B:
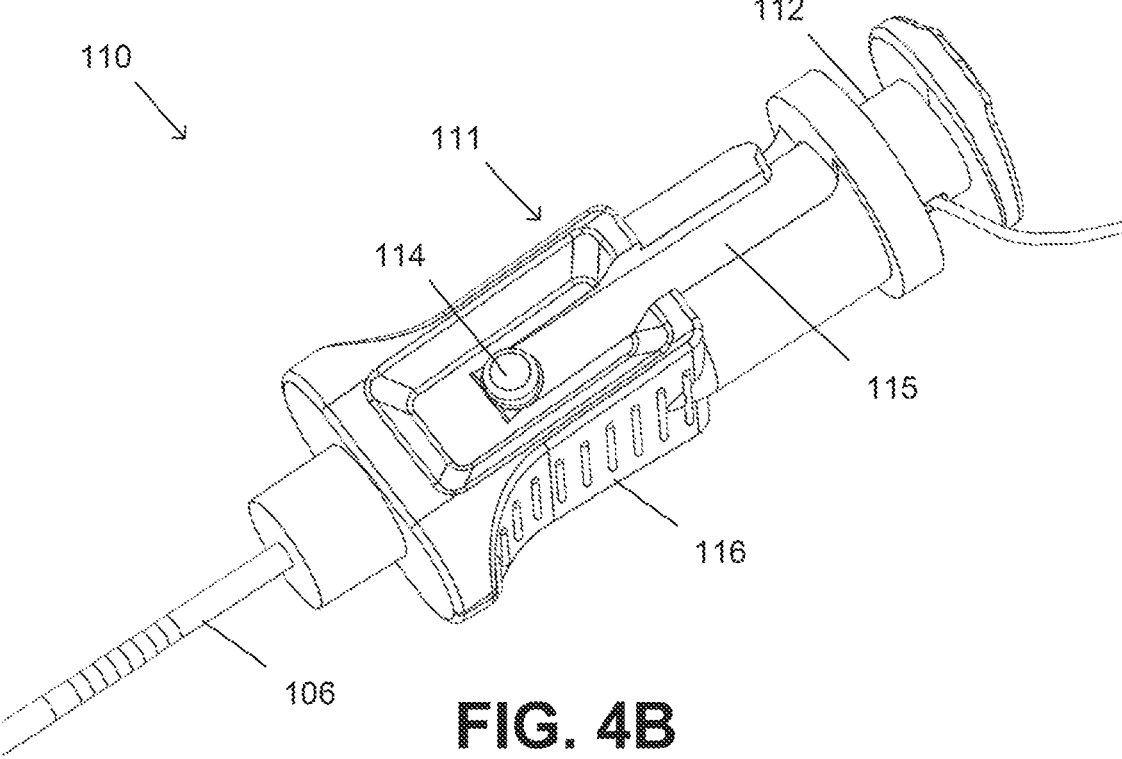
FIG. 4B is a side view of a handle assembly in the deployed position in one variation.
Figure 4C:
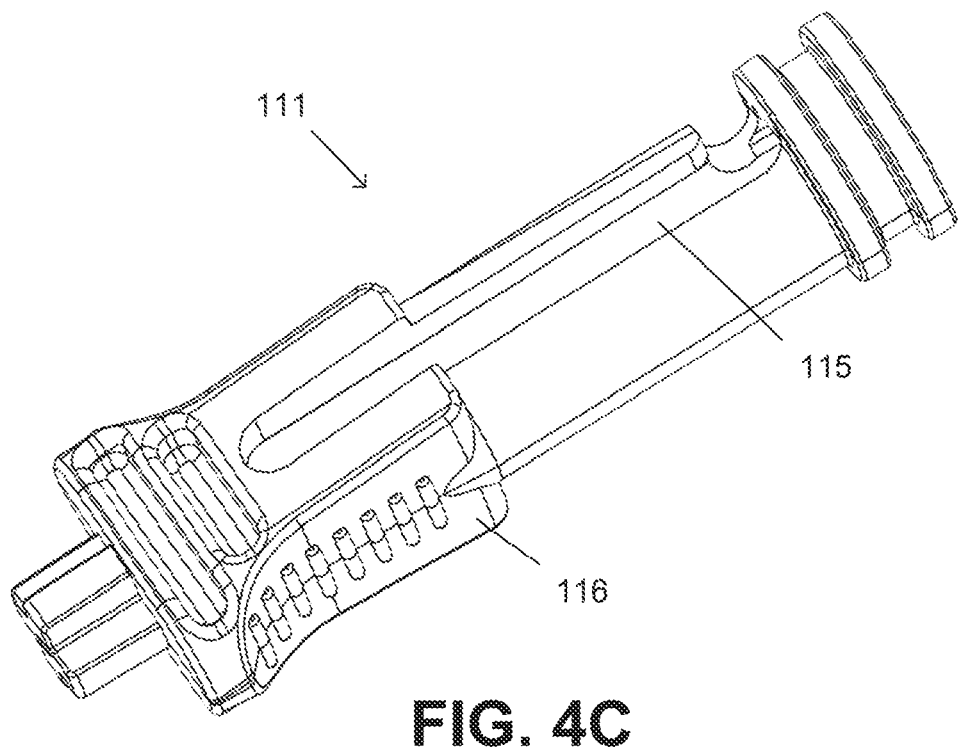
FIG. 4C is a side view of a handle body in one variation.

The tissue marking device 100 may further include a handle assembly 110. As seen in FIG. 1 and FIGS. 4A-4E, the handle assembly 110 includes a handle body 111, a plunger 112, a needle 106, and a stylet 108. As seen in FIGS. 4A-4C, the handle body 111 may include a grip 116 at the distal end of the handle body 111, a hollow longitudinal barrel, and a guide 115 extending longitudinally along a length of the handle body 111. The plunger 112 is operable to fit within the barrel of the handle body 111 and includes a locking mechanism 114 at its distal end operable to fit within the guide 115. The hook assembly 105 is initially contained within the needle 106 of the handle assembly 110 until it is deployed by the handle assembly 110 once near the target tissue. The handle assembly 110, by way of the needle 106, is configured to enter the breast and place the hook assembly 105 in the target tissue.

The needle 106 has a lumen that is open on a first end and a second end. In a variation, the needle 106 is a 16 gauge needle. In a variation, the needle 106 is a 17 gauge needle. In a variation, the needle 106 is an 18 gauge needle. In a variation, the needle 106 is a 19 gauge needle. In a variation, the needle 106 is a 20 gauge needle. In a variation, the needle 106 is at least 5 cm long. In a variation, the needle 106 is at least 7 cm long. In a variation, the needle 106 is at least 8 cm long. In a variation, the needle 106 is at least 10 cm long. In a variation, the needle 106 is at least 12 cm long. In a variation, the needle 106 is at least 14 cm long. In a variation, the needle 106 is at least 16 cm long. In a variation, the needle 106 is at least 20 cm long. In a variation, the needle 106 is less than 20 cm long. The needle 106 is attached to the distal end of the handle body 111. The needle 106 may be reversibly or irreversibly attached to the distal end of the handle body 111.

The stylet 108 may be a tube that is open on a first end and second end. The stylet 108 is configured to sit within the needle 106 and hold the thread 104 within its lumen. The first end of the stylet 108 may extend into the handle body 111 and the second end of the stylet 108 may rest on or near the proximal end of the hook body 102. FIGS. 2A and 2B show the second end of the stylet 108 surrounding the thread 104 and near the proximal end of the hook body 102. In a variation, the first end of the stylet 108 is connected to the distal end of the plunger 112.

The stylet 108 may have a diameter sufficient to fit within the lumen of the needle 106 while being the same diameter or smaller than the diameter of the hook body 102. This allows for the stylet 108 to push on the proximal end of the hook body 102 to push the hook body 102 out of the needle and into the target tissue. In a variation, the stylet 108 may have an outer diameter less than the diameter of the lumen of the needle 106. In a variation, the stylet 108 may have an outer diameter of less than 1.5 mm. In a variation, the stylet 108 may have an outer diameter of less than 1 mm. In a variation, the stylet 108 may have an outer diameter of less than 0.75 mm. In a variation, the stylet 108 may have an outer diameter of less than 0.5 mm. In a variation, the stylet 108 may have an outer diameter of at least 0.5 mm. In a variation, lumen of the stylet 108 may have a diameter of at least 0.25 mm. In a variation, lumen of the stylet 108 may have a diameter of less than 0.5 mm. In a variation, lumen of the stylet 108 may have a diameter of less than 0.75 mm. In a variation, lumen of the stylet 108 may have a diameter of less than 1 mm.

The stylet 108 may have a length that is at least the length of the needle 106. In a variation, the stylet 108 is longer than the needle 106. In a variation, the stylet 108 is at least 5 cm long. In a variation, the stylet 108 is at least 7 cm long. In a variation, the stylet 108 is at least 8 cm long. In a variation, the stylet 108 is at least 10 cm long. In a variation, the stylet 108 is at least 12 cm long. In a variation, the stylet 108 is at least 14 cm long. In a variation, the stylet 108 is at least 16 cm long. In a variation, the stylet 108 is at least 20 cm long. In a variation, the stylet 108 is less than 20 cm long.

The handle body is designed to minimize size and weight of the device. It has an ergonomic grip and the hook assembly can be deployed with a simple turn of the handle. As seen in FIG. 4C, the handle body 111 includes a grip 116 at the distal end of the handle body 111, a hollow longitudinal barrel, and a guide 115 extending longitudinally along a length of the handle body 111. The handle body may be made of molded plastic in one variation.

Figure 4D:
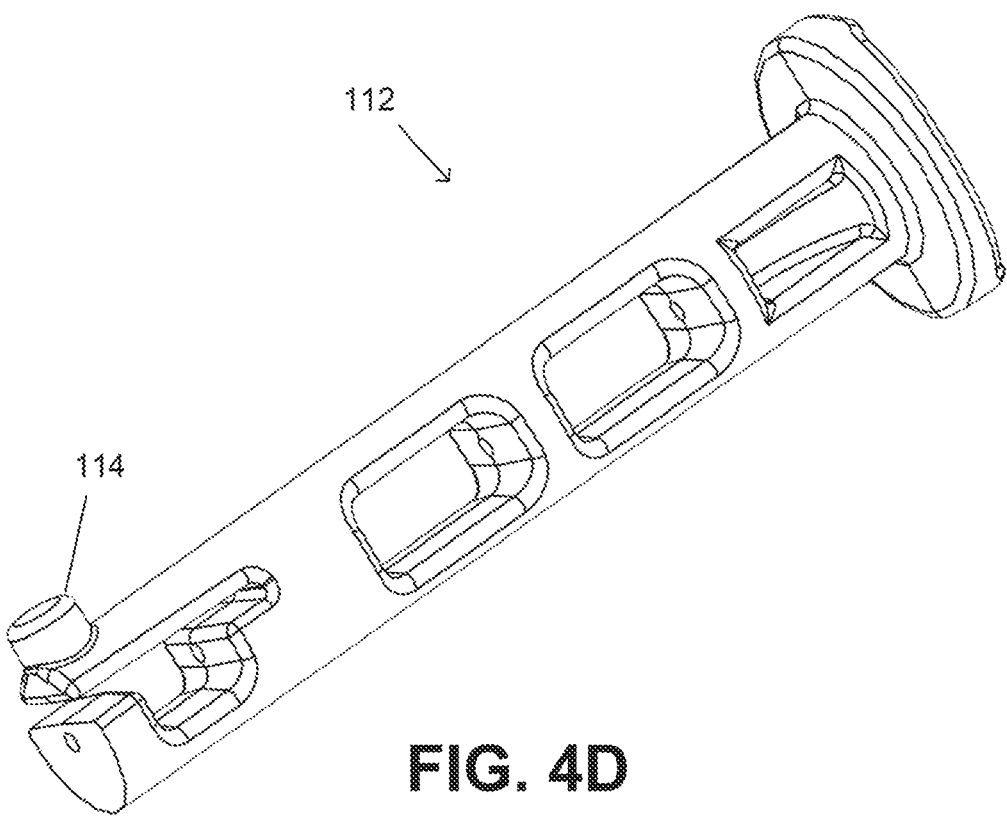
FIG. 4D is a side view of a plunger in one variation.
Figure 4E:
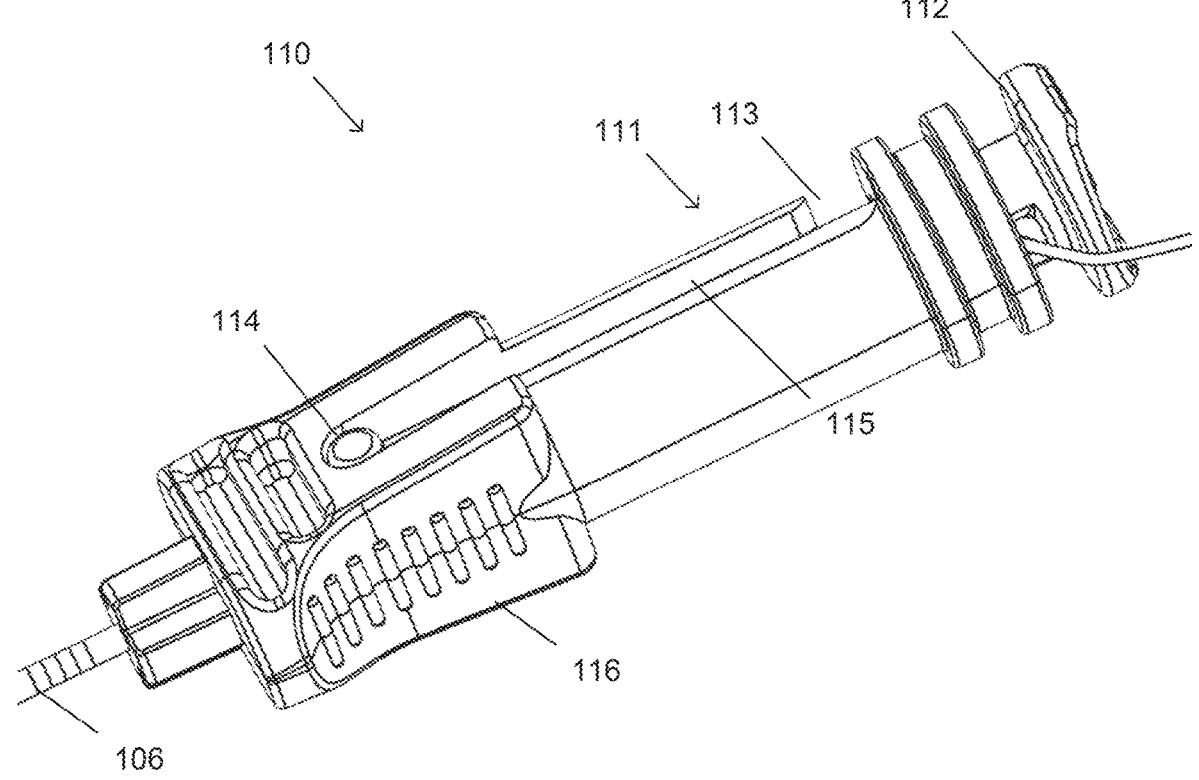
FIG. 4E is a side view of a handle assembly in the deployed position in one variation.

As seen in FIG. 4D, the plunger 112 includes a locking mechanism 114 at its distal end operable to fit within the guide 115 of the handle body 111. As seen in FIG. 4E, the plunger 112 is sized to fit inside the barrel of the handle body 111. The plunger 112 extends the length of the handle body 111, protrudes out the proximal end of the handle body 111, and connects to the stylet 108 at its distal end within the handle body 111. The plunger 112 is configured to actuate between two distinct positions, an extended position and a depressed position. FIG. 4A shows the plunger 112 in the extended position when the handle assembly 110 is loaded with the hook assembly 105. In particular, FIG. 4A shows the thread 104 loaded through the handle body 111 and plunger 112. When the plunger 112 is in the extended position, the hook body 102 remains in the needle 106 and the thread remains in the stylet 108, needle 106, and hook body 111/plunger 112. FIG. 4B shows the plunger 112 in the depressed position when the hook assembly 105 has been deployed. When the plunger 112 is pushed from the extended position to the depressed position, the hook body 102 is pushed by the stylet 108 the distance the plunger 112 is pressed, and therefore, the hook body 102 extends past the second end of the needle 106 by the same distance. Therefore, when placing the needle 106 in the target tissue, it is known what distance the hook body 102 will be pushed past the second end of the needle 106 when the plunger 112 is depressed and the hook body 102 is deployed.

The handle body 111 may further include an opening for receiving a proximal end of the thread. In one variation, the plunger may further include an opening 118, as seen in FIG. 4A, that receives the excess end of the thread 104. In other variations, the opening 118 may be located on any portion of the handle body 111 and/or the plunger 112.

The handle body 111 or the plunger 112 may further include a locking mechanism 114. In a variation, the locking mechanism 114 is near the distal end of the plunger 112. The locking mechanism 114 may be a protrusion that fits within the guide 115 extending at least a portion of the length of the handle body 111. The locking mechanism 114 may be in a locked or unlocked position. When in the locked position, the locking mechanism 114 may be located within a recession 113 on the handle body 111 perpendicular to the guide 115 at the proximal end of the guide 115. To move the locking mechanism 114 to the unlocked position, the locking mechanism 114 is moved or rotated to be outside of the recession 113 to be within the guide 115. Because the locking mechanism is on the plunger, the plunger is moved or rotated such that the locking mechanism is outside the recession and within the guide to unlock the handle. In some variations, the recession has a length at least half the circumference of the handle body such that the plunger has to rotate at least 180° to unlock. The locking mechanism 114 may be connected to the plunger 112 such that the locking mechanism 114 prevents the actuation of the plunger 112 when the locking mechanism 114 is in the locked position. FIG. 4A shows the locking mechanism in a locked position. FIG. 4B shows the locking mechanism in an unlocked position. The length of the guide 115 may be compatible with the length of the plunger 112 and the desired distance that the plunger may be pushed to deploy the hook assembly 105.

The locking mechanism 114 prevents the hook assembly 105 from being accidentally deployed during assembly, shipment, and insertion of the needle. Because the tissue marking device 100 is a single use, non-removable device, the locking mechanism 114 is necessary to prevent accidental deployment until it is confirmed that the hook assembly will be deployed in the desired location of the target tissue.

In a variation, the handle body 111 may further include a grip 116. In a variation, the grip 116 may be a two finger grip for easy manipulation by the physician, as seen in FIGS. 4A-4C. Further, the handle body 111 may be lightweight, such that the weight of the handle body attached to the needle 106 does not affect the movement or placement of the hook assembly 105.

In use, the hook assembly 105 is seated in the second end of the needle 106 and stylet 108 such that the hooks 101 and retention mechanism 107 are in the compressed configuration. The handle assembly 110, by way of the needle 106, is forced in the breast until the second end of the needle 106 reaches the target tissue. The locking mechanism 114 is rotated from the recession 113 into the guide 115 to be in the unlocked position. The plunger 112 is pressed by the thumb or another finger of the user. The first end of the stylet 108 is then pressed by the plunger 112 causing the hook body 102 to extend past the second end of the needle 106, open/deploy the hooks 101, and embed in the target tissue. The needle 106 and stylet 108 are removed from the tissue using the handle body 111, leaving the thread 104 protruding from the skin and attached to the hook body 102.

Figure 5:
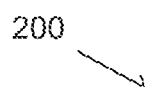
FIG. 5 is a diagram of a method of using of the tissue marking device in one variation.
Figure 5:
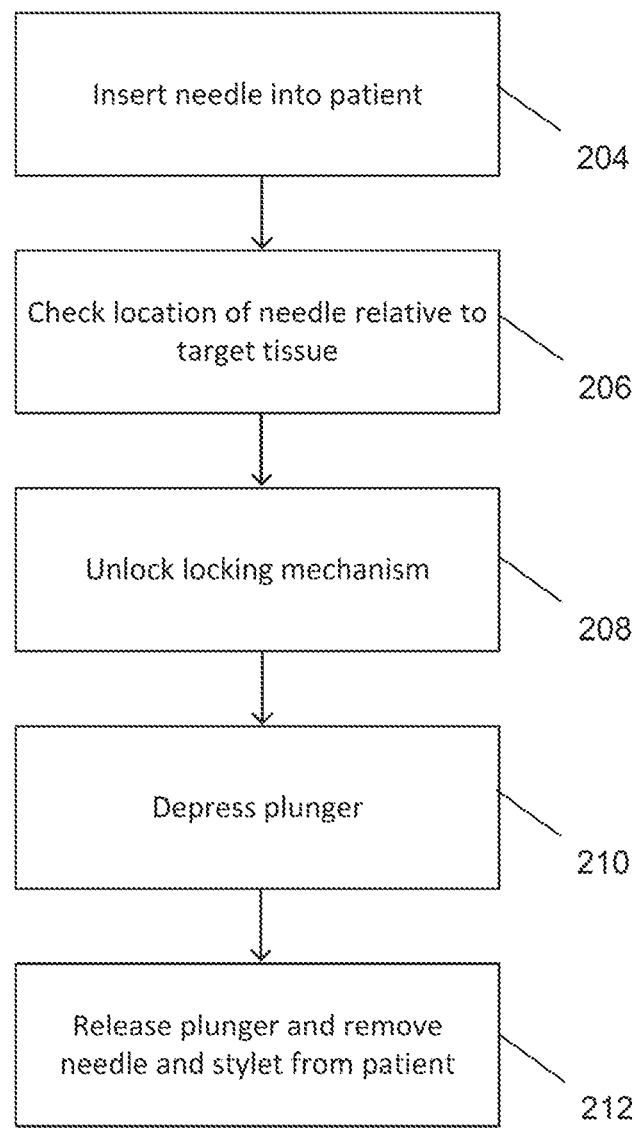

A description of a method for marking tissue for removal using a tissue marking device, as illustrated in FIG. 5, is disclosed herein. The method shown in FIG. 5 is provided by way of example, as there are a variety of ways to carry out the method. Additionally, while the example methods are illustrated with a particular order of blocks, those of ordinary skill in the art will appreciate that FIG. 5 and the blocks shown therein can be executed in any order that accomplishes the technical advantages of the present disclosure and can include fewer or more blocks than illustrated. Each block shown in FIG. 5 represents one or more processes, methods or subroutines, carried out in the example method.

Referring now to FIG. 5, the method of using the tissue marking device 100 is depicted in one variation. Method 200 includes inserting the needle with the compressed hook assembly in a patient so that the hook body is near a target tissue at steps 204 and 206, unlocking the locking mechanism at step 208, depressing the plunger to extend the hook body past the needle and embed in the target tissue at step 210, and removing the needle and stylet from the patient at step 212. In a variation, the method 200 may further include leaving the thread exposed on the surface of the skin. The exposed thread may then be secured to the skin. In some variations, the method may further include loading the hook assembly in the handle assembly prior to inserting the needle into the patient. Loading the hook assemble in the handle assembly may include loading/inserting the hook body into the needle and loading/inserting the thread through the stylet, needle, and plunger within the handle body. The hooks and retention mechanism of the hook body may need to be physically compressed to be loaded within the needle.

The use of the tissue marking device allows for the safe separation of treatment days. The separation of treatment days provides time for the hook assembly to be properly placed and then patient can return on a different day for surgery instead of being rushed to surgery on the same day and being severely restricted on movement for fear of the marker migrating. In addition, the separation of treatment days overcomes the inefficiencies created trying to coordinate radiology, surgery, operating room, and patient physical location when the localization and surgery are on the same day.

Figure 6:
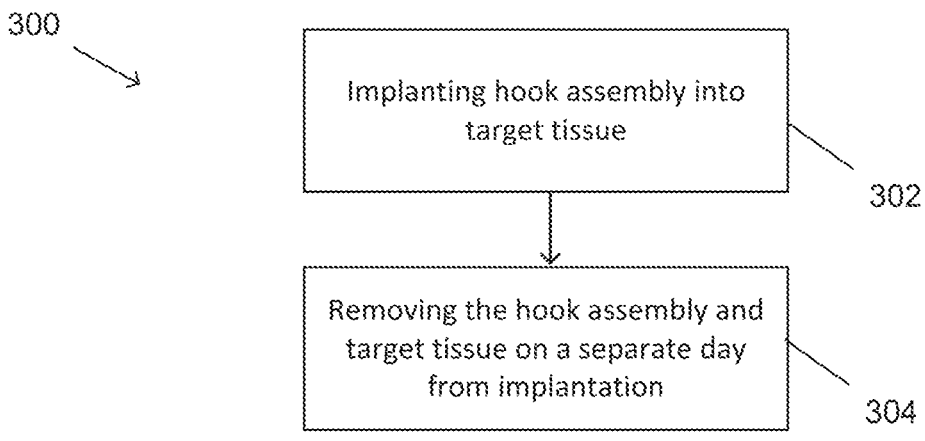
FIG. 6 is a diagram of a method of using of marking a target tissue in one variation.

In another variation, FIG. 6 provides a method for marking tissue for removal using a tissue marking device. The method shown in FIG. 6 is provided by way of example, as there are a variety of ways to carry out the method. Additionally, while the example methods are illustrated with a particular order of blocks, those of ordinary skill in the art will appreciate that FIG. 6 and the blocks shown therein can be executed in any order that accomplishes the technical advantages of the present disclosure and can include fewer or more blocks than illustrated. Each block shown in FIG. 6 represents one or more processes, methods or subroutines, carried out in the example method.

Referring now to FIG. 6, the method of implanting and removing the hook assembly 105 of the tissue marking device 100 is depicted in one variation. Method 300 includes implanting the hook assembly of the tissue marking device into a target tissue of a patient at step 302 and removing the hook assembly and target tissue on a separate day from implantation at step 304. In a variation, the hook assembly is operable to absorb compression forces without migrating within the target tissue such that re-localization/re-implantation would be required. In a variation, the hook assembly is operable to allow the patient to have surgery to remove the hook assembly on a separate day from localization/implantation. The ability to absorb compression forces may permit the patient to participate in normal activity between the time of localization/implantation of the hook assembly and the time of surgery to remove the target tissue. Non-limiting examples of normal activity include sleeping (face down if desired), sexual activity, taking care of loved ones (for example, kids), exercising, and/or lifting heaving objects.

Unlike conventional wire marker devices, the hook assembly can be embedded in a target tissue and still allow a patient to perform most normal activities. This allows the hook assembly to be placed far in advance of the surgery. The structure of the hook body with hooks and retention mechanism may allow for the hook assembly to flex with the patient's movements and thus not migrate within the target tissue. In a variation, the hook body may only migrate up to 15 mm from its original placement location. In a variation, the hook body may only migrate up to 10 mm from its original placement location. In a variation, the hook body may only migrate up to 8 mm from its original placement location. In a variation, the hook body may only migrate up to 6 mm from its original placement location. In a variation, the hook body may only migrate up to 5 mm from its original placement location. In a variation, the hook body may only migrate up to 4 mm from its original placement location. In a variation, the hook body may only migrate up to 2 mm from its original placement location. In a variation, the hook body may only migrate up to 1 mm from its original placement location. In a variation, the hook body may only migrate up to 0.5 mm from its original placement location. In addition, the thread may further allow for the patient's movements to not affect the hook body placement. The flexible thread may impart less tension on the hook body as compared to a standard wire such that it flexes instead of pulling on the hook body. In some variations, the hook assembly may have a pull force of greater than 380 g.

In some variations, the method may further include surgically removing the hook assembly and target tissue on a separate day from when the hook assembly was implanted. In a variation, the hook assembly may be placed up to 24 hours before surgery. In a variation, the hook assembly may be placed more than 24 hours before surgery. In a variation, the hook assembly may be placed up to 2 days before surgery. In a variation, the hook assembly may be placed up to 5 days before surgery. In a variation, the hook assembly may be placed up to 8 days before surgery. In a variation, the hook assembly may be placed up to 10 days before surgery. In a variation, the hook assembly may be placed up to 12 days before surgery. In a variation, the hook assembly may be removed at least 24 hours after implantation. In a variation, the hook assembly may be removed up to 2 days after implantation. In a variation, the hook assembly may be removed up to 5 days after implantation. In a variation, the hook assembly may be removed up to 8 days after implantation. In a variation, the hook assembly may be removed up to 10 days after implantation. In a variation, the hook assembly may be removed up to 12 days after implantation.

A tissue marking device comprising: a hook assembly having a compressed configuration and a deployed configuration, the hook assembly comprising: a hook body comprising at least two hooks; and a thread connected to the hook body; and a handle assembly for positioning the hook assembly in a targeted tissue comprising: a handle body having a proximal end and a distal end; a needle having a lumen with an open first end and a second end; and a stylet having a lumen with an open first end and a second end, wherein the hook body and the stylet are within the lumen of the needle and the thread is within the lumen of the stylet when the hook assembly is in the compressed configuration.

A tissue marking device comprising: a hook body having a proximal end and a distal end, the hook body comprising at least two hooks, wherein the hook body has a compressed configuration and a deployed configuration.

A tissue marking device comprising: a hook body comprising at least two hooks; a metal thread crimped or welded to the proximal end of the hook body.

A tissue marking device comprising: a handle assembly comprising: a handle body having a proximal end and a distal end; a needle having a lumen with an open first end and a second end, the needle lumen configured to contain a hook body in a compressed configuration; and a stylet having a lumen with an open first end and a second end, the stylet configured to be within the lumen of the needle and the stylet lumen configured to contain a thread connected to the hook body.

The handle body comprises a plunger and a locking mechanism. The first end of the stylet is connected to the plunger such that pressing the plunger extends the hook body into the target tissue. The handle body further comprises a recession and guide for positioning the locking mechanism in a locked and unlocked position, respectively. The hook body comprises two hooks. The hook body comprises three hooks. The tissue hook body comprises at least two hooks separated by 180°, 120°, 90°, 45°, or a combination thereof. The hook body comprises at least two hooks having a straight configuration or curved configuration. The hook body comprises a laser cut nitinol tube. The thread is selected from a chromium cobalt, stainless steel, nitinol, or Kevlar thread. The thread is crimped or welded to a proximal end of the hook body. The hook body has at least one radiopaque marker. The thread has at least one radiopaque marker. The first end of the needle is connected to the distal end of the handle body.

A method of marking a target tissue in a patient comprising: inserting a tissue marking device into a patient, the tissue marking device comprising: a hook assembly comprising a hook body with at least two hooks and a thread; and a handle assembly comprising a stylet, a needle, and a handle body comprising a locking mechanism and a plunger; confirming the location of the needle such that the hook body is near the target tissue; unlocking the locking mechanism on the handle body; depressing the plunger to extend the hook body past the needle and open the at least two hooks to embed the hook body in the target tissue; and removing the needle and the stylet from the patient.

The method further comprises loading the hook assembly into the handle assembly. The method further comprises securing the thread to the patient's skin. The method further comprises having the patient return at least 24 hours later for surgery. The patient returns up to 12 days later for surgery. The hook assembly has a compressed configuration and a deployed configuration. The hook body and the stylet are within the lumen of the needle and the thread is within the lumen of the stylet when the hook assembly is in the compressed configuration. The handle body further comprises a recession and guide for positioning the locking mechanism in a locked and unlocked position, respectively. The hook body comprises two hooks. The hook body comprises three hooks. The hook body comprises at least two hooks separated by 180°, 120°, 90°, 45°, or a combination thereof. The hook body comprises at least two hooks having a straight configuration or curved configuration. The hook body comprises a laser cut nitinol tube. The thread is selected from a chromium cobalt, stainless steel, nitinol, or Kevlar thread. The thread is crimped or welded to a proximal end of the hook body. The hook body has at least one radiopaque marker. The thread has at least one radiopaque marker. The target tissue is within the patient's breast.

EXAMPLES

Example 1: Pull Force Testing

Resistance capability towards traction force of the tissue marking device was examined. Turkey breast was used as a substitute for softer human breast tissue. Tissues were examined at room temperature. The tissues were compressed in a mammography unit using a compression force of 10 N. Four tissue marking devices (DFC "H" Hook) with a four arm configuration (two distal hooks and two proximal hooks) were inserted about 5 cm into the compressed tissues. Traction force was applied in each case for 1 second using an analogue Spring Scale starting with 50 g of pulling force (1000 g=9.81 Newton). Pulling force was increased in steps of 50 g. Table 1 below shows the pulling force observed to pull the device out of the tissue.

TABLE 1

| DFC Hook Testing rev.O2 | | |
| --- | --- | --- |
| Sample # | Hook Description | Pull Force (Grams) |
| 2 | DFC (Nitinol-"H" Hook-rev.O2) | 391.86 |
| 3 | DFC (Nitinol-"H" Hook-rev.O2) | 385.68 |
| 4 | DFC (Nitinol-"H" Hook-rev.O2) | 380.42 |
| 5 | DFC (Nitinol-"H" Hook-rev.O2) | 415.12 |
| | * Average Pull Force | 393.27 |
| | Standard Deviation | 15.30 |

In general, the pull forces measured with the tissue marking devices tracked with or were greater than the localization devices currently available (see Kaul, et al., Dislocability of Localization Devices for Nonpalpable Breast Lesions: Experimental Results, Radiology Research and Practice, 2014).

Example 2: Compression Testing

To test any migration of the hook assembly in response to compression forces, a 3D printed test system with a motor and an electric cycle counter was created to hold and compress a breast equivalent gel. A hook body with a four arm configuration (two distal hooks and two proximal hooks) was injected into 1 inch of breast equivalent gel and pre and post compression measurements were taken with a caliper. The gel with the implanted hook body was compressed by 30% for each compression. A set of 100 compressions was performed and then a set of 1,000 compressions was performed to generally simulate normal activity for a patient. For each set, the hook body was assessed for movement from the position of the hook body before testing. Table 2 shows the movement observed before and after compressions.

TABLE 2

| Number of Cycles | Position of Hook before Testing | Position of Hook after Testing |
| --- | --- | --- |
| 100 | 9.55 mm | 9.56 mm |
| 1000 | 9.56 mm | 9.59 mm |

The four arm hook body only migrated 0.01 mm after 100 compression cycles and 0.03 mm after 1000 compression cycles. Therefore, the four arm hook demonstrated minimal migration such that it may absorb compressions encountered in normal activity between the time of placing the hook assembly and surgery to remove the hook assembly and target tissue.

The particular variations disclosed above are illustrative only, as the variations may be modified and practiced in different but equivalent manners apparent to those skilled in the art having the benefit of the teachings herein. It is therefore evident that the particular variations disclosed above may be altered or modified, and all such variations are considered within the scope and spirit of the application. Accordingly, the protection sought herein is as set forth in the description. Although the present variations are shown above, they are not limited to just these variations, but are amenable to various changes and modifications without departing from the spirit thereof. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed variations teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A tissue marking device, comprising:
a hook assembly, comprising:
a hook body;
a thread connected to the hook body; and
a handle assembly operable for positioning the hook assembly in a targeted tissue, the handle assembly comprising:
a handle body having a proximal end and a distal end, the handle body defining a guide extending longitudinally from the proximal end along a length of the handle body and a recession extending perpendicularly from the guide at the proximal end, at least a portion of the guide defining a window from an interior of the handle body to an exterior of the handle body;
a needle having a lumen with an open first end and a second end;
a plunger operable to fit within the handle body, the plunger having a locking mechanism rotatable relative to the handle body between a locked position and an unlocked position such that rotation of the plunger relative to the handle body causes the locking mechanism to move from the locked position to the unlocked position, the locking mechanism comprising a protrusion disposed at a distal end of the plunger; and
a stylet having a lumen with an open first end and a second end,
wherein the plunger is actuatable between an extended position and a depressed position by moving the plunger longitudinally within the guide of the handle body when the locking mechanism is rotated relative to the handle body into the unlocked position,
wherein the locking mechanism restricts actuation of the plunger from the extended position to the depressed position when the locking mechanism is rotated relative to the handle body into the locked position,
wherein the hook body and the stylet are within the lumen of the needle when the plunger is in the extended position,
wherein the hook body extends past the needle when the plunger is in the depressed position,
wherein the protrusion is within the guide and extends at least partially into the window defined by the guide such that the protrusion is visible from the exterior of the handle body when the locking mechanism is in the unlocked position, and
wherein the protrusion is within the recession when the locking mechanism is in the locked position.

2. The tissue marking device of claim 1, wherein the plunger is at least partially disposed within the handle body and protrudes from the proximal end of the handle body.

3. The tissue marking device of claim 1, wherein the thread extends through the stylet, the needle, the handle body, and the plunger when the plunger is in the extended position.

4. The tissue marking device of claim 1, wherein the handle body further comprises a proximal wall portion disposed at the proximal end of the handle body between the protrusion and a proximal end of the plunger, the proximal wall portion of the handle body configured to limit movement of the plunger to between the extended position and the depressed position and to prevent removal of the plunger from the proximal end of the handle body.

5. The tissue marking device of claim 4, wherein rotation of the plunger from the locked position to the unlocked position causes the protrusion to move from the recession to the guide.

6. The tissue marking device of claim 1, wherein the first end of the stylet is connected to the plunger.

7. The tissue marking device of claim 6, wherein actuating the plunger from the extended position to the depressed position extends the hook body into the targeted tissue.

8. The tissue marking device of claim 1, wherein the handle body includes a grip at the distal end thereof.

9. The tissue marking device of claim 1, wherein the handle body is made of a molded plastic.

10. The tissue marking device of claim 1, wherein the plunger extends along a length of the handle body.

11. The tissue marking device of claim 1, wherein the plunger connects the second end of the stylet to the handle body.

12. The tissue marking device of claim 1, wherein the hook body defines an opening configured to receive a proximal end of the thread.

13. The tissue marking device of claim 1, wherein the plunger defines an opening configured to receive an excess end of the thread.

14. The tissue marking device of claim 1, wherein the recession has a length at least half a circumference of the handle body.

15. The tissue marking device of claim 14, wherein moving the locking mechanism from the locked position to the unlocked position includes rotating the plunger at least 180° relative to the handle body.

16. The tissue marking device of claim 1, wherein the guide has a length sufficient to allow the hook body to extend past the needle when the plunger is in the depressed position.

17. A method of marking a targeted tissue in a patient, the method comprising:
inserting the tissue marking device of claim 1 into the patient;
confirming a location of the needle such that the hook body is near the targeted tissue;
moving the locking mechanism from the locked position to the unlocked position;
actuating the plunger to move from the extended position to the depressed position to extend the hook body past the needle and embed the hook body in the targeted tissue; and
removing the needle and the stylet from the patient.

18. The method of claim 17, wherein moving the locking mechanism from the locked position to the unlocked position includes rotating the plunger relative to the handle body.

19. The method of claim 18, wherein rotating the plunger from the locked position to the unlocked position causes the protrusion to move from the recession to the guide.

* * * * *